US00PP23809P2

(12) United States Plant Patent
Dümmen

(10) Patent No.: US PP23,809 P2
(45) Date of Patent: Aug. 6, 2013

(54) *PELARGONIUM* PLANT NAMED 'DUEBELVIDAR'

(50) Latin Name: *Pelargonium peltatum*
Varietal Denomination: Duebelvidar

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 105 days.

(21) Appl. No.: 13/373,736

(22) Filed: Nov. 28, 2011

(51) Int. Cl.
*A01H 5/00* (2006.01)

(52) U.S. Cl.
USPC ..... Plt./332

(58) Field of Classification Search
USPC ..... Plt./332
See application file for complete search history.

*Primary Examiner* — June Hwu
(74) *Attorney, Agent, or Firm* — C. A. Whealy

(57) ABSTRACT

A new and distinct cultivar of Ivy Geranium plant named 'Duebelvidar', characterized by its compact, upright to outwardly spreading plant habit; moderately vigorous growth habit; freely basal branching habit; freely flowering habit; large dark red-colored single flowers; and good garden performance.

1 Drawing Sheet

Botanical designation: *Pelargonium peltatum.*
Cultivar denomination: 'DUEBELVIDAR'.

BACKGROUND OF THE INVENTION

The present invention relates to a new and distinct cultivar of Ivy Geranium plant, botanically known as *Pelargonium peltatum*, and hereinafter referred to by the name 'Duebelvidar'.

The new Ivy Geranium plant is a product of a planned breeding program conducted by the Inventor in Rheinberg, Germany. The objective of the breeding program is to create new freely-branching Ivy Geranium plants with dark green-colored leaves and attractive flowers.

The new Ivy Geranium plant originated from a cross-pollination made by the Inventor in July, 2008 in Rheinberg, Germany of a proprietary selection of *Pelargonium peltatum* identified as code number F-1815-18, not patented, as the female, or seed, parent with a proprietary selection of *Pelargonium peltatum* identified as code number P05-1510-4, not patented, as the male, or pollen, parent. The new Ivy Geranium plant was discovered and selected by the Inventor as a single flowering plant from within the progeny of the stated cross-pollination in a controlled greenhouse environment in Rheinberg, Germany in May, 2011.

Asexual reproduction of the new Ivy Geranium plant by vegetative terminal cuttings in a controlled greenhouse environment in Rheinberg, Germany since June, 2011 has shown that the unique features of this new Ivy Geranium plant are stable and reproduced true to type in successive generations.

SUMMARY OF THE INVENTION

Plants of the new Ivy Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duebelvidar'.

These characteristics in combination distinguish 'Duebelvidar' as a new and distinct Ivy Geranium plant:

1. Compact, upright to outwardly spreading plant habit.
2. Moderately vigorous growth habit.
3. Freely basal branching habit.
4. Freely flowering habit.
5. Large dark red-colored single flowers.
6. Good garden performance.

Plants of the new Ivy Geranium differ primarily from plants of the female parent selection in the following characteristics:

1. Plants of the new Ivy Geranium have darker red-colored flowers than plants of the female parent selection.
2. Plants of the new Ivy Geranium have single flowers whereas plants of the female parent selection have double flowers.

Plants of the new Ivy Geranium differ primarily from plants of the male parent selection in the following characteristics:

1. Plants of the new Ivy Geranium are more compact than plants of the male parent selection.
2. Plants of the new Ivy Geranium have single flowers whereas plants of the male parent selection have double flowers.

Plants of the new Ivy Geranium can be compared to plants of *Pelargonium peltatum* 'Royal Red', not patented. In side-by-side comparisons conducted in Rheinberg, Germany, plants of the new Ivy Geranium differed primarily from plants of 'Royal Red' in the following characteristics:

1. Plants of the new Ivy Geranium had shorter internodes than plants of 'Royal Red'.
2. Plants of the new Ivy Geranium had larger inflorescences than plants of 'Royal Red'.
3. Plants of the new Ivy Geranium had darker red-colored flowers than plants of 'Royal Red'.
4. Plants of the new Ivy Geranium had single flowers whereas plants of 'Royal Red' had double flowers.

BRIEF DESCRIPTION OF THE PHOTOGRAPH

The accompanying colored photograph illustrates the overall appearance of the new Ivy Geranium plant showing the colors as true as it is reasonably possible to obtain in colored reproductions of this type. Colors in the photograph may differ slightly from the color values cited in the detailed botanical description which accurately describe the colors of the new Ivy Geranium plant. The photograph comprises a side perspective view of a typical flowering plant of 'Duebelvidar' grown in a container.

DETAILED BOTANICAL DESCRIPTION

The aforementioned photograph and following observations and measurements describe plants grown during the summer in 12-cm containers in a glass-covered greenhouse in Rheinberg, Germany and under cultural practices which closely approximate commercial Pelargonium production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium peltatum* 'Duebelvidar'.

Parentage:

*Female, or seed, parent*.—Proprietary selection of *Pelargonium peltatum* identified as code number F-1815-18, not patented.

*Male or pollen parent*.—Proprietary selection of *Pelargonium peltatum* identified as code number P05-1510-4, not patented.

Propagation:

*Type*.—By vegetative terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*General appearance*.—Compact, upright to outwardly spreading plant habit; uniformly rounded; densely foliated.

*Growth and branching habit*.—Moderately vigorous growth habit; freely basal branching habit with about three basal branches developing per plant.

*Plant height to top of flower umbels*.—About 29 cm.

*Plant height to top of foliar plane*.—About 25.5 cm.

*Plant width*.—About 23.5 cm.

*Lateral branches*.—Length: About 23.8 cm. Diameter: About 7 mm. Internode length: About 2.7 cm. Texture: Pubescent. Strength: Moderately strong. Color: Close to 144B.

Foliage description:

*Arrangement*.—Alternate; simple.

*Length*.—About 5.7 cm.

*Width*.—About 6.7 cm.

*Shape*.—Reniform.

*Apex*.—Acute.

*Base*.—Peltate.

*Margin*.—Entire to crenate.

*Venation pattern*.—Palmate.

*Texture, upper surface*.—Pubescent.

*Texture, lower surface*.—Smooth, glabrous.

*Color*.—Developing leaves, upper surface: Close to 146A. Developing leaves, lower surface: Close to 144A. Fully expanded leaves, upper surface: Close to 147A; venation, close to 147A. Fully expanded leaves, lower surface: Close to 146A; venation, close to 144A. Zonation pattern: Not discernible.

*Petiole*.—Length: About 3.1 cm. Diameter: About 2.5 mm. Texture, upper and lower surfaces: Smooth, glabrous. Color, upper surface: Close to 146A. Color, lower surface: Close to 146B.

Flower description:

*Flower arrangement*.—Single rotate flowers arranged in rounded hemispherical umbels arising from apical leaf axils; umbels displayed above the foliage on moderately strong peduncles; flowers face mostly upright.

*Fragrance*.—None detected.

*Quantity of flowers*.—Freely flowering habit, about ten flowers per umbel.

*Flowering season*.—Year-round under greenhouse conditions; in outdoor nurseries and gardens in Germany, flowering is continuous from spring throughout the summer; plants begin to flower about eight weeks after planting.

*Flower longevity*.—Individual flowers last about five to seven days on the plant; flowers persistent.

*Umbel height*.—About 4.4 cm.

*Umbel diameter*.—About 8.9 cm.

*Flower diameter*.—About 4.5 cm by 4.7 cm.

*Flower depth* (*height*).—About 2.5 cm.

*Flower buds*.—Length: About 1.6 cm. Diameter: About 7 mm. Shape: Ovoid. Color: Close to 46A.

*Petals*.—Quantity per flower: Five, arranged in a single whorl. Length: About 2.6 cm. Width: About 1.8 cm. Shape: Obovate. Apex: Rounded. Base: Attenuate. Margin: Sinuate. Texture, upper and lower surfaces: Smooth, glabrous. Color: When opening, upper surface: Close to 46A. When opening, lower surface: Close to 45B. Fully opened, upper surface: Close to 45A; color becoming closer to 187A with development. Fully opened, lower surface: Close to 45B; central stripping close to 187A; color becoming closer to 187A with development.

*Petaloids*.—None observed.

*Sepals*.—Quantity per flower: Five, arranged in a single whorl. Length: About 1.4 cm. Width: About 4 mm. Shape: Ensiform. Apex: Apiculate. Base: Attenuate. Margin: Entire. Color, upper surface: Close to 146B. Color, lower surface: Close to 146A.

*Peduncle* (*umbel stem*).—Length: About 10.5 cm. Diameter: About 3.5 mm. Strength: Moderately strong. Texture: Smooth, glabrous. Color: Close to 144A.

*Pedicel* (*individual flower stem*).—Length: About 2.1 cm. Diameter: About 2 mm. Strength: Moderately strong. Texture: Smooth, glabrous. Color: Close to 146B.

*Reproductive organs*.—Androecium: Stamen quantity per flower: About eight. Filament length: About 9.5 mm. Filament color: Close to 65A. Anther length: About 3 mm. Anther shape: Oval. Anther color: Close to 59A. Pollen amount: Moderate. Pollen color: Close to 28A. Gynoecium: Pistil quantity per flower: One. Pistil length: About 1 cm. Stigma shape: Parted. Stigma color: Close to 60A. Style length: About 2 mm. Style color: Close to 145D. Ovary color: Close to 147D.

*Seeds and fruits*.—Seed and fruit development have not been observed on plants of the new Ivy Geranium.

Disease & pest resistance: Plants of the new Ivy Geranium have not been observed to be resistant to pathogens and pests common to Ivy Geraniums.

Garden performance: Plants of the new Ivy Geranium have been observed have good garden performance and to tolerate rain, wind, and temperatures ranging from about 5° C. to about 40° C.

It is claimed:

1. A new and distinct Ivy Geranium plant named 'Duebelvidar' as illustrated and described.

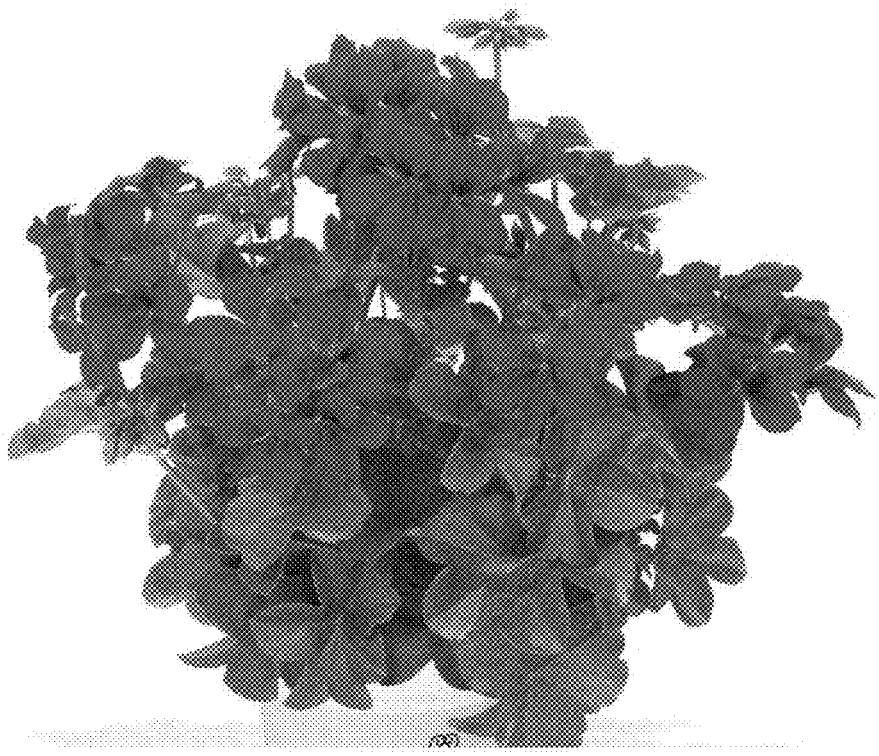

* * * * *